United States Patent
Housman et al.

(10) Patent No.: US 9,872,688 B2
(45) Date of Patent: Jan. 23, 2018

(54) SOFT TISSUE REPAIR METHOD

(71) Applicant: Smith & Nephew, Inc., Memphis, TN (US)

(72) Inventors: Mark E. Housman, North Attleboro, MA (US); Paul S. Vincuilla, Brockton, MA (US); Nikhil N. Verma, Chicago, IL (US); Scott Trenhaile, Belvidere, IL (US)

(73) Assignee: Smith & Nephew, Inc., Memphis, TN (US)

( * ) Notice: Subject to any disclaimer, the term of this patent is extended or adjusted under 35 U.S.C. 154(b) by 96 days.

(21) Appl. No.: 14/716,252

(22) Filed: May 19, 2015

(65) Prior Publication Data

US 2015/0250487 A1   Sep. 10, 2015

Related U.S. Application Data

(63) Continuation of application No. 12/725,686, filed on Mar. 17, 2010, now Pat. No. 9,060,748.

(60) Provisional application No. 61/161,124, filed on Mar. 18, 2009.

(51) Int. Cl.
| | | |
|---|---|---|
| *A61B 17/17* | (2006.01) | |
| *A61B 17/00* | (2006.01) | |
| *A61B 17/56* | (2006.01) | |
| *A61B 17/88* | (2006.01) | |
| *A61B 17/86* | (2006.01) | |
| *A61B 17/04* | (2006.01) | |
| *A61F 2/08* | (2006.01) | |

(Continued)

(52) U.S. Cl.
CPC .............. *A61B 17/17* (2013.01); *A61B 17/00* (2013.01); *A61B 17/0401* (2013.01); *A61B 17/1684* (2013.01); *A61B 17/1714* (2013.01); *A61B 17/1739* (2013.01); *A61B 17/28* (2013.01); *A61B 17/56* (2013.01); *A61B 17/8645* (2013.01); *A61B 17/8875* (2013.01); *A61F 2/0805* (2013.01); *A61F 2/0811* (2013.01); *A61B 17/1764* (2013.01); *A61B 17/864* (2013.01); *A61B 17/8897* (2013.01); *A61B 2017/0409* (2013.01); *A61B 2017/0412* (2013.01); *A61B 2017/0445* (2013.01); *A61B 2017/0464* (2013.01); *A61B 2017/1778* (2013.01); *A61F 2002/0841* (2013.01); *A61F 2002/0858* (2013.01); *A61F 2002/0888* (2013.01)

(58) Field of Classification Search
CPC .. A61B 17/17; A61B 2017/0445; A61B 17/00
See application file for complete search history.

(56) References Cited

U.S. PATENT DOCUMENTS

| | | | | |
|---|---|---|---|---|
| D374,283 S | * | 10/1996 | Michelson | D24/133 |
| D397,436 S | * | 8/1998 | Michelson | D24/133 |

(Continued)

*Primary Examiner* — Christian Sevilla
(74) *Attorney, Agent, or Firm* — Norman F. Hainer, Jr.

(57) ABSTRACT

The present disclosure relates to an instrument and method of manipulating soft tissue during a soft tissue repair procedure. The instrument and related method may include use of a handle and a shaft coupled to the handle, the shaft including a proximal portion and a distal portion, wherein the distal portion of the shaft comprises a tip including at least two prongs and a channel located between the prongs.

23 Claims, 18 Drawing Sheets

(51) Int. Cl.
*A61B 17/28* (2006.01)
*A61B 17/16* (2006.01)

(56) References Cited

U.S. PATENT DOCUMENTS

2008/0009678 A1* 1/2008 Ritland .............. A61B 17/1757
          600/201
2008/0065020 A1* 3/2008 Ralph ................ A61B 17/1686
          604/164.11

* cited by examiner

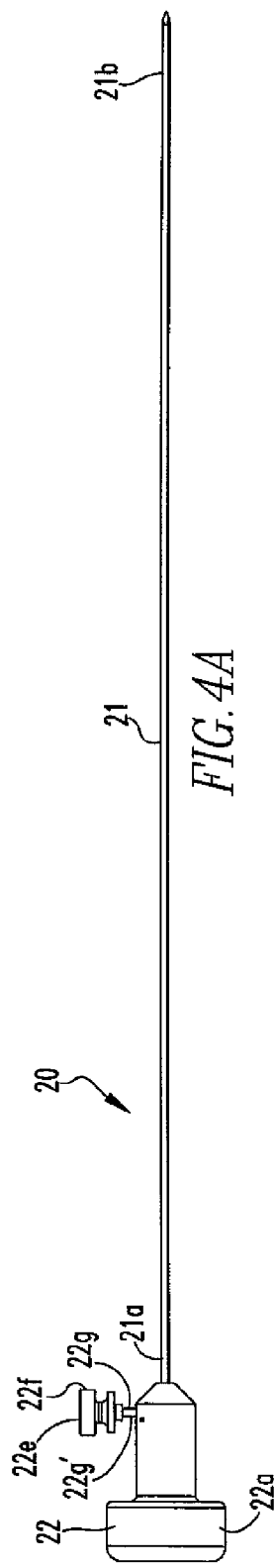
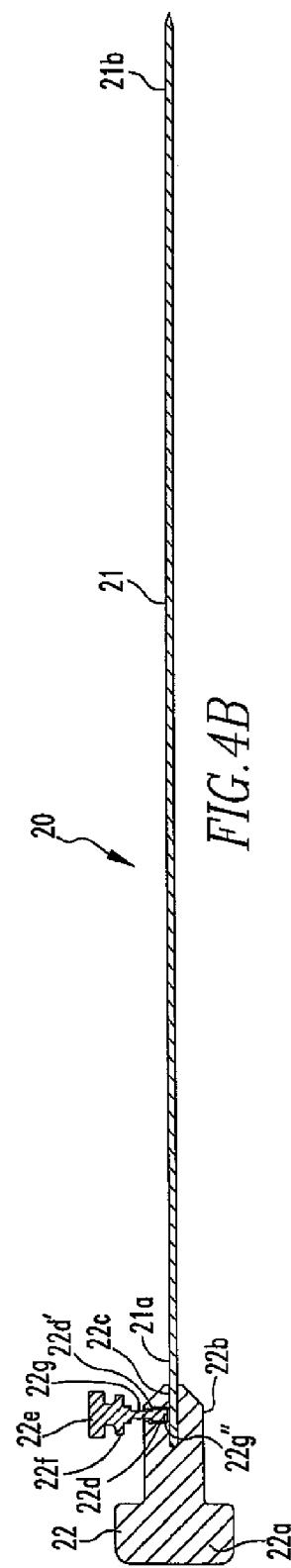
FIG. 4A
FIG. 4B

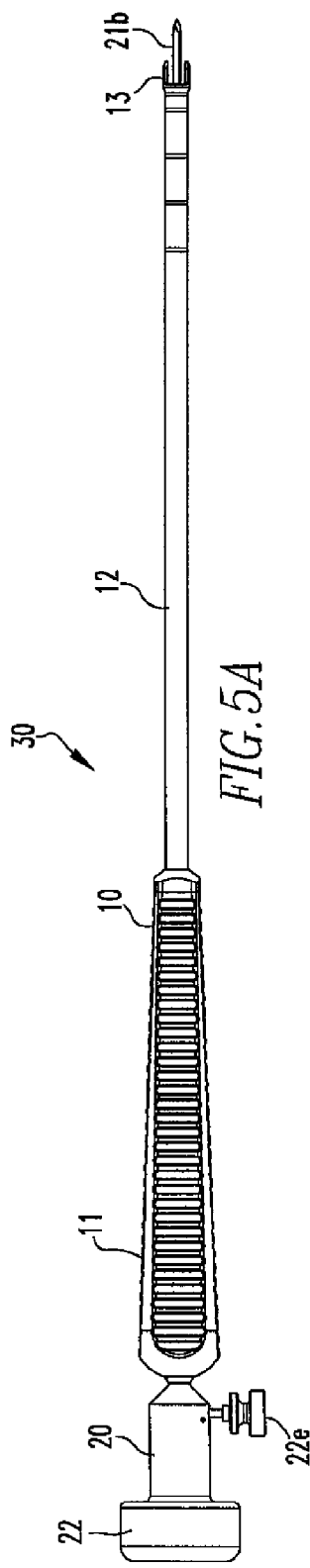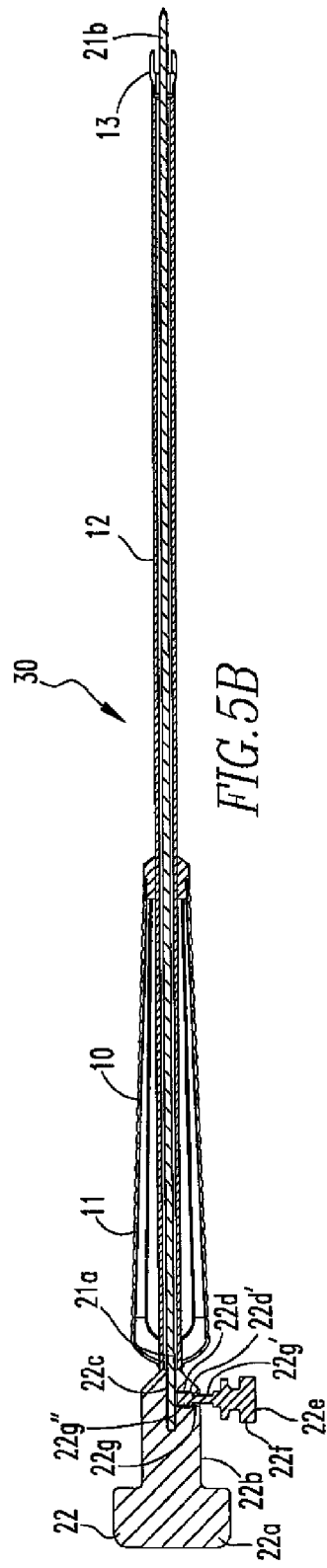

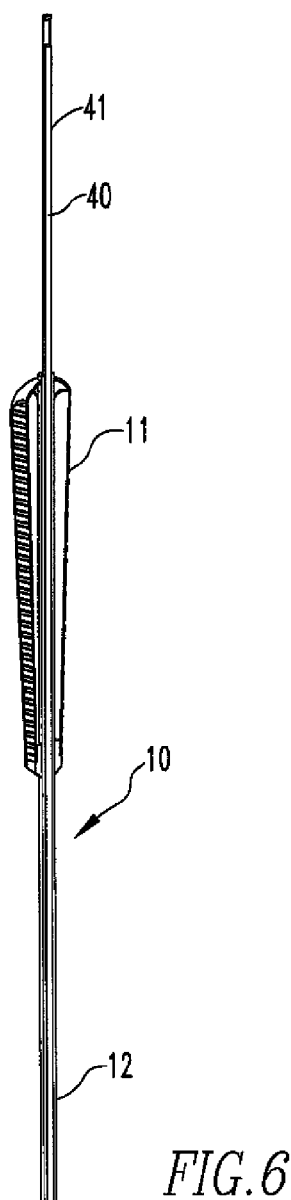
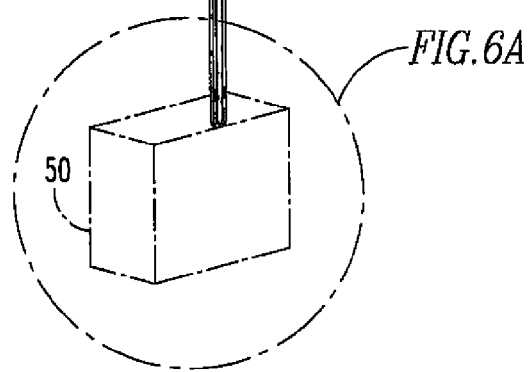
FIG.6
FIG.6A

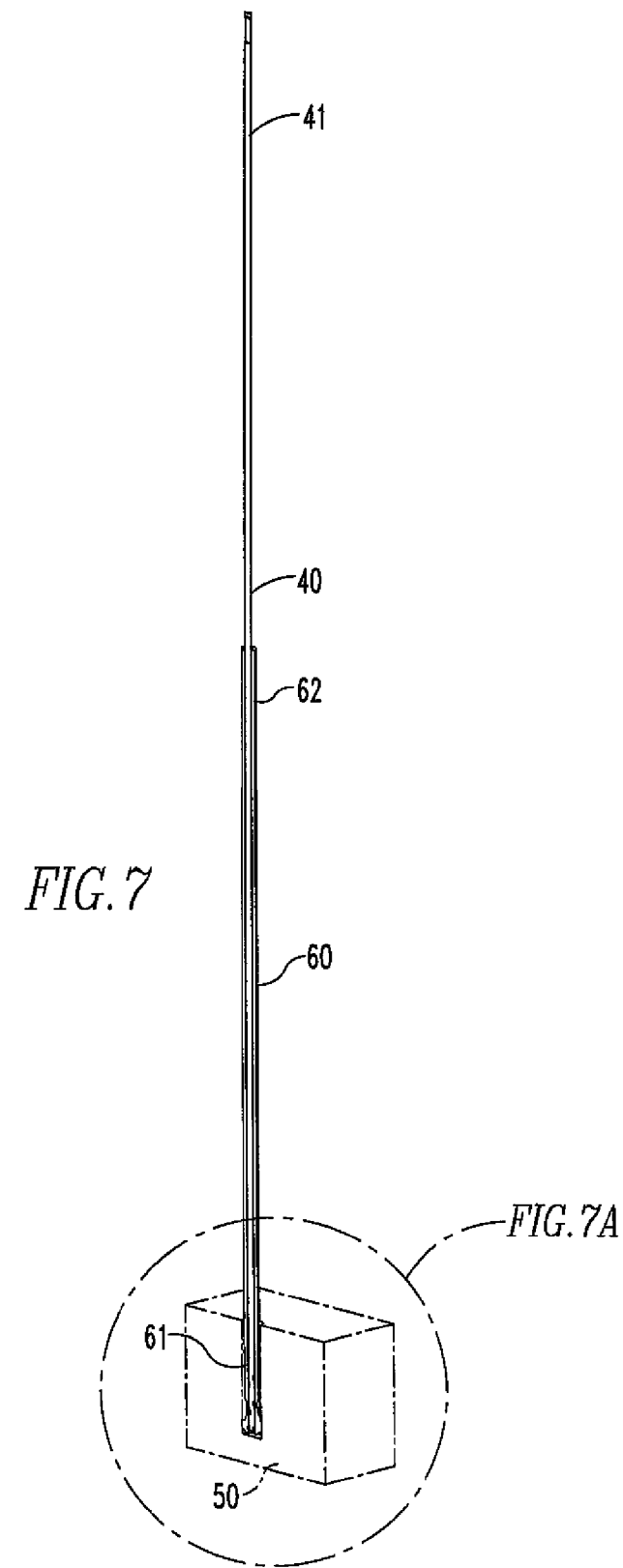

SOFT TISSUE REPAIR METHOD

CROSS-REFERENCE TO RELATED APPLICATIONS

This application is a continuation of U.S. patent application Ser. No. 12/725,686, filed Mar. 17, 2010, which claims priority to U.S. Provisional Patent Application No. 61/161,124, filed Mar. 18, 2009, and is related to U.S. patent application Ser. No. 14/642,337, filed on Mar. 9, 2015, which is a divisional of U.S. patent application Ser. No. 12/725,686; the disclosures of all of which are incorporated by reference herein in their entirety.

BACKGROUND

Field of Technology

The present disclosure relates to a device and method for manipulating soft tissue during a soft tissue repair procedure.

Related Art

During repair of soft tissue, such as biceps tenodesis repair, the biceps tendon is placed and temporarily secured in a prepared hole in the humerus prior to final fixation of the tendon via a fixation device, such as an interference screw. Devices that would accomplish this temporary placement and fixation are needed.

SUMMARY

In one aspect, the present disclosure relates to an instrument for manipulating soft tissue during a soft tissue repair procedure. The instrument includes a handle; and a shaft coupled to the handle, the shaft including a proximal portion and a distal portion, wherein the distal portion of the shaft comprises a tip including at least two prongs and a channel located between the prongs. In an embodiment, the instrument is cannulated. In another embodiment, the distal portion includes marks, the marks representing a measured distance from an end of at least one of the prongs to the marks. In yet another embodiment, an outer diameter of the tip is between about 4.5 mm to about 5.5 mm.

In another aspect, the present disclosure relates to a method of tissue repair. The method includes creating a hole in bone; placing the soft tissue over the hole; providing a cannulated instrument for inserting the soft tissue into the hole, the instrument including a handle and a shaft coupled to the handle, the shaft including a proximal portion and a distal portion, wherein the distal portion includes a tip including at least two prongs and a channel located between the prongs; inserting the soft tissue into the hole via use of the instrument, wherein the soft tissue is housed within the channel; and inserting a fixation device into the hole to fix the soft tissue to the bone. In an embodiment, the method further includes inserting a guide assembly through the cannulation of the instrument and into the bone prior to inserting the fixation device into the hole, the guide assembly comprising a guide wire and a vice coupled to the guide wire, the guide assembly inserted through the cannulation until a bottom portion of the vice engages with the handle. In yet another embodiment, the method further includes inserting the fixation device into the hole via use of the guide wire.

In a further aspect, the present disclosure relates to a soft tissue manipulator assembly. The manipulator assembly includes a soft tissue manipulator instrument having a handle, a shaft coupled to the handle, a tip coupled to the shaft, and a cannulation extending an entire length of the instrument; and a guide assembly disposed within the cannulation, the assembly comprising a guide wire and a vice coupled to the guide wire, the vice including a bottom portion and a top portion, the bottom portion in engagement with the handle.

In yet a further aspect, the present disclosure relates to a kit. The kit includes a soft tissue manipulator instrument including a handle, a shaft coupled to the handle, and a tip coupled to the shaft; a guide wire; a vice including a top portion and a bottom portion, the bottom portion having a channel and a hole extending perpendicular to the channel; and a fixation device. In an embodiment, the kit further includes a drill bit; a reamer; and a driver.

Embodiments of the invention may include a method of attaching a biceps tendon to a humerus. Methods may include creating a hole in the humerus of a first diameter; severing a proximal end of the biceps tendon; pushing a portion of the biceps tendon into the hole with an instrument that captures the biceps tendon at a distal end of the instrument; inserting a distal portion of a guide wire though the biceps tendon and into humerus in the hole in the humerus; and inserting a fixation device over the guide wire to fix the biceps tendon to the humerus.

Still other embodiments of the invention may include a method of tissue repair that includes creating a hole in a bone of a first diameter; pushing a portion of soft tissue into the hole with an instrument that captures the soft tissue in a channel adjacent to one or more prongs of a tip at a distal end of the instrument; inserting a distal portion of a guide wire though the soft tissue and in the hole in the bone; and inserting a fixation device over the guide wire to fix the soft tissue to the bone.

Embodiments of the invention may be directed to an instrument with a proximal end and a distal end, the instrument configured to manipulate soft tissue during a soft tissue repair procedure. The instrument may include a cannulated instrument body and a first prong coupled to the cannulated instrument body, wherein the first prong is the most distal element of the instrument and is offset from the cross-sectional center of the cannulated instrument body. The instrument may also include markings on the instrument representing a measured distance from a distal end of the first prong to the markings.

Other embodiments of the invention include an instrument with a proximal end and a distal end, the instrument configured to manipulate soft tissue during a soft tissue repair procedure. The instrument may include a cannulated instrument body, a first prong coupled to the cannulated instrument body, wherein the first prong is the most distal element of the instrument and is offset from the cross-sectional center of the cannulated instrument body, and a second prong coupled to the cannulated instrument body opposite from the first prong to form a channel between the first prong and the second prong, wherein the channel aligns at least in part with a cannulation of the cannulated instrument body. The first prong and the second prong may be rounded and blunted at their respective distal ends to not readily penetrate bone when pushed against the bone.

Yet other embodiments includes an instrument with a proximal end and a distal end, the instrument configured to manipulate soft tissue during a soft tissue repair procedure. The instrument may have a cannulated instrument body, a fork means at a distal end of the instrument for capturing soft tissue between a first prong of the fork and a second prong of the fork and aligning the soft tissue with a cannulation of the cannulated instrument body, and a depth determining means for measuring a distance from a distal end of the fork means to markings on the instrument.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings:

FIG. 4A shows a side view of the guide assembly of the present disclosure.

FIG. 4B shows a cross-sectional view of the guide assembly of FIG. 4A.

FIG. 5A shows a side view of the soft tissue manipulator assembly of the present disclosure.

FIG. 5B shows a cross-sectional view of the soft tissue manipulator assembly of FIG. 5A.

FIGS. 6-6A show the soft tissue manipulator instrument of FIG. 1 and a drill bit disposed within the instrument prior to creation of a hole in bone.

FIGS. 7-7A show the use of a reamer to increase the diameter of the hole created by the drill bit of FIGS. 6-6A.

DETAILED DESCRIPTION OF THE EMBODIMENTS

The following description of the preferred embodiment(s) is merely exemplary in nature and is in no way intended to limit the disclosure, its application, or uses.

Figure 1:
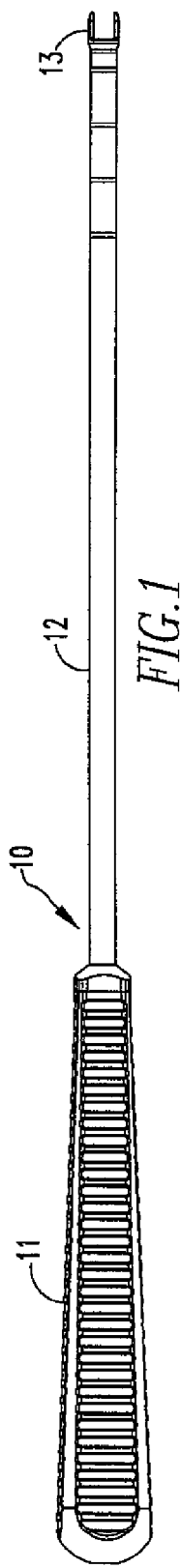
FIG. 1 shows a side view of the soft tissue manipulator instrument of the present disclosure.
Figure 1A:
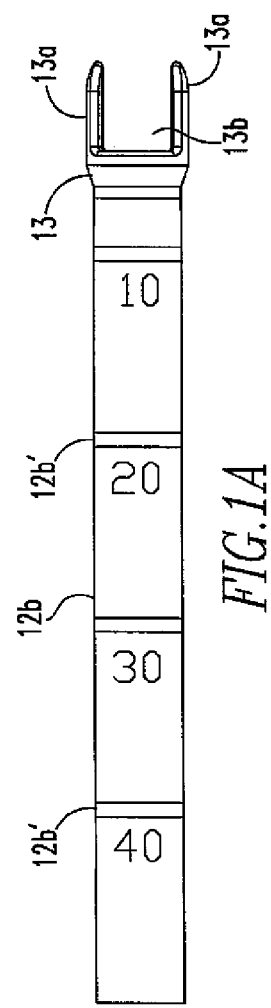
FIG. 1A shows an expanded view of the distal portion of the shaft of the instrument of FIG. 1.
Figure 2:
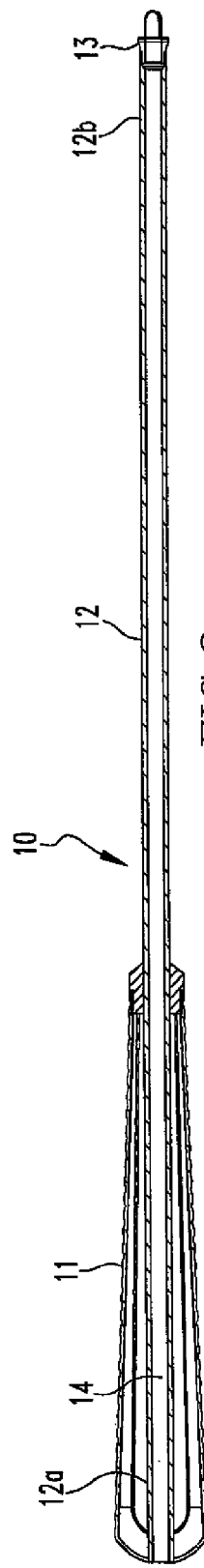
FIG. 2 shows a cross-sectional view of the instrument of FIG. 1.
Figure 3A:
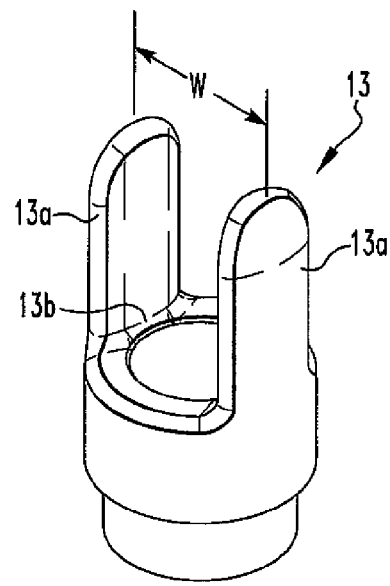
FIGS. 3A-3C each show isometric views of the tip of the instrument of FIG. 1.
Figure 3B:
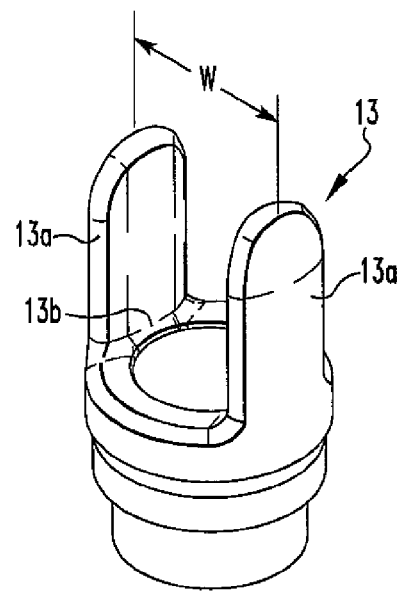
Figure 3C:
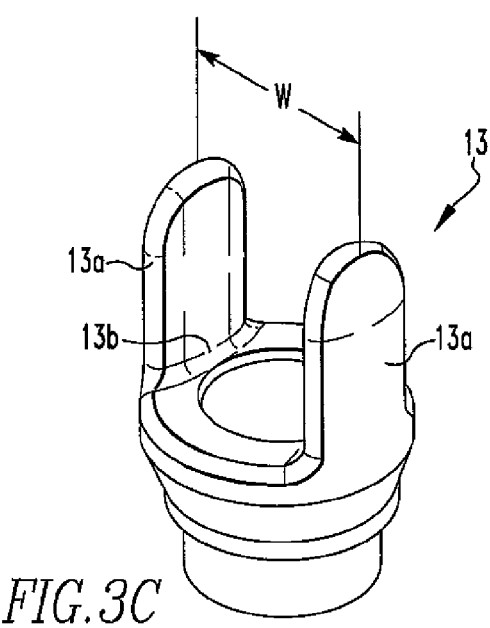

FIGS. 1 and 2 show the soft tissue manipulator instrument 10 of the present disclosure. The instrument 10 includes a handle 11 and a shaft 12 coupled to the handle 11. The instrument 10 includes a cannulation 14 that extends the entire length of the instrument 10. The shaft 12 includes a proximal portion 12a coupled to the handle 11 and a distal portion 12b. The distal portion 12b includes a tip 13 having prongs 13a and a channel 13b located between the prongs 13b. FIGS. 3A-3C show three tips 13, all of which have a different outer width W. For the purposes of this disclosure, the widths W of the tips 13 are 4.5 mm, 5.0 mm, and 5.5 mm. However, other widths W may be used. As will be described further below, the choice of which instrument 10 to use will depend on the diameter of the soft tissue that is being repaired. In addition, FIG. 1A shows markings 12b', and numbers correlating with those markings, located at the distal portion 12b of the shaft 12. As will be further described below, the markings 12b' are used to determine the depth of a bone hole during repair.

FIGS. 4A and 4B show the guide assembly 20 of the present disclosure. The assembly 20 includes a guide wire 21 having a proximal portion 21a and a distal portion 21b. Coupled to the proximal portion 21a of the guide wire 21 is a wire vice 22. The vice 22 includes a top portion 22a, a bottom portion 22b, a channel 22c that houses the proximal portion 21a of the guide wire 21, a hole 22d extending perpendicular to the channel 22c and having threads on an inner surface 22d' of the hole 22d, and a knob assembly 22e housed within the hole 22d. The assembly 22e includes a knob 22f and a pin 22g coupled to the knob 22f. The pin 22g includes a proximal portion 22g' coupled to the knob 22f and a distal portion 22g" having threads that are engaged with the threads on the inner surface 22d' of the hole 22d. Prior to use of the guide assembly 20 during repair, the proximal portion 21a of the guide wire 21 is disposed within the channel 22c of the vice 22 and the knob 22f of the knob assembly 22e is rotated until the distal portion 22g" of the pin 22g abuts the proximal portion 21a of the guide wire 21, thereby coupling the assembly 22e to the proximal portion 21a of the guide wire 21.

FIGS. 5A and 5B show the soft tissue manipulator assembly 30 of the present disclosure. As will be further described below, the assembly 30 is used to insert tissue into bone.

Figure 6A:
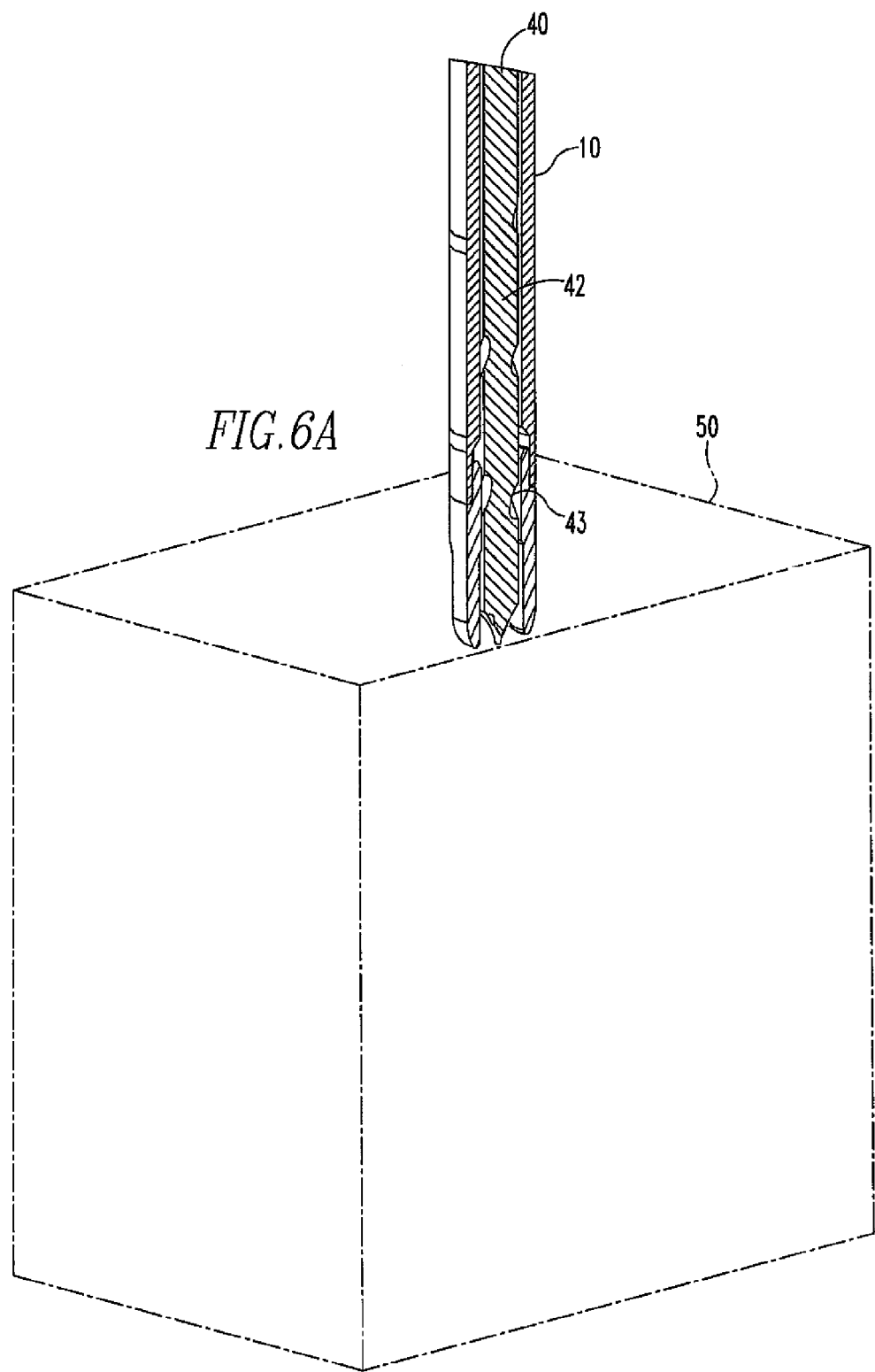

FIGS. 6-12 show a method of soft tissue repair. FIGS. 6 and 6A show the soft tissue instrument 10 and a drill bit 40 disposed within the cannulation 14 of the instrument 10. The drill bit 40 includes a proximal portion 41 and a distal portion 42 having threads 43. The instrument 10 is used as a guide for placement of the drill bit 40 into bone 50. Once the drill bit 40 is disposed in the instrument 10, as shown in FIG. 6, a drill (not shown) is coupled to the proximal portion 41 of the bit 40 and is operated to rotate the bit 40 and advance the bit 40 into the bone 50. For the purposes of this disclosure, the drill bit 40 is 2.4 mm in diameter, but other diameter drill bits may be used. Once the bit 40 is advanced into the bone 50, the instrument 10 is removed while the drill bit 40 is maintained in bone 50.

Figure 7A:
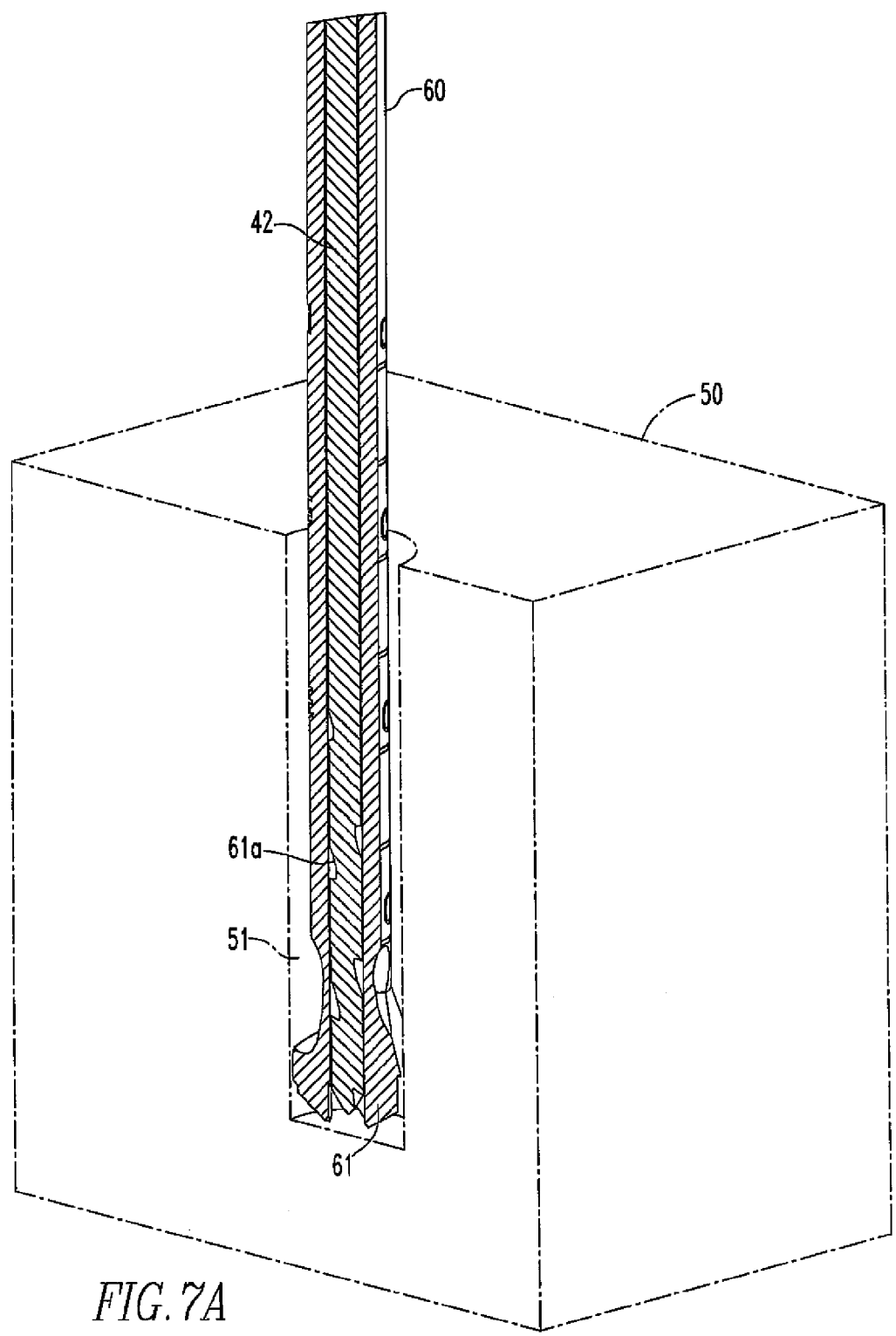

As shown in FIGS. 7 and 7A, a cannulated reamer 60 is disposed over the drill bit 40 and is used to provide the create a hole 51 in the bone 50. The reamer 60 includes a distal portion 61 having threads 61a and a proximal portion 62.

Once the reamer 60 is disposed over the drill bit 40, a drill (not shown) is then coupled to the proximal portion 62 and operated to rotate the reamer 60 and advance the reamer 60 into the bone 50, thereby creating the hole 51. For the purposes of this disclosure, the diameter of the reamer 60 is 6-8 mm, however the diameter is dependent on the diameter of the soft tissue that is placed within the hole 50, as will be further described below. Therefore, other diameter reamers may be used. In addition, the distal portion 61 of the reamer 60 may include number markings, similar to the markings 12b' described above, for measuring the depth of the reamer 60 as it is being advanced into the bone 50.

Figure 8:
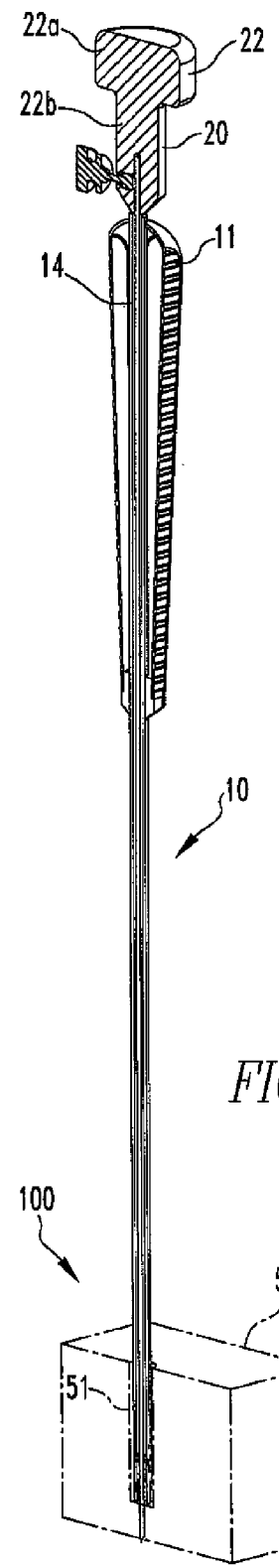
FIG. 8 shows the insertion of the soft tissue manipulator assembly of FIG. 5A in bone.
Figure 8A:
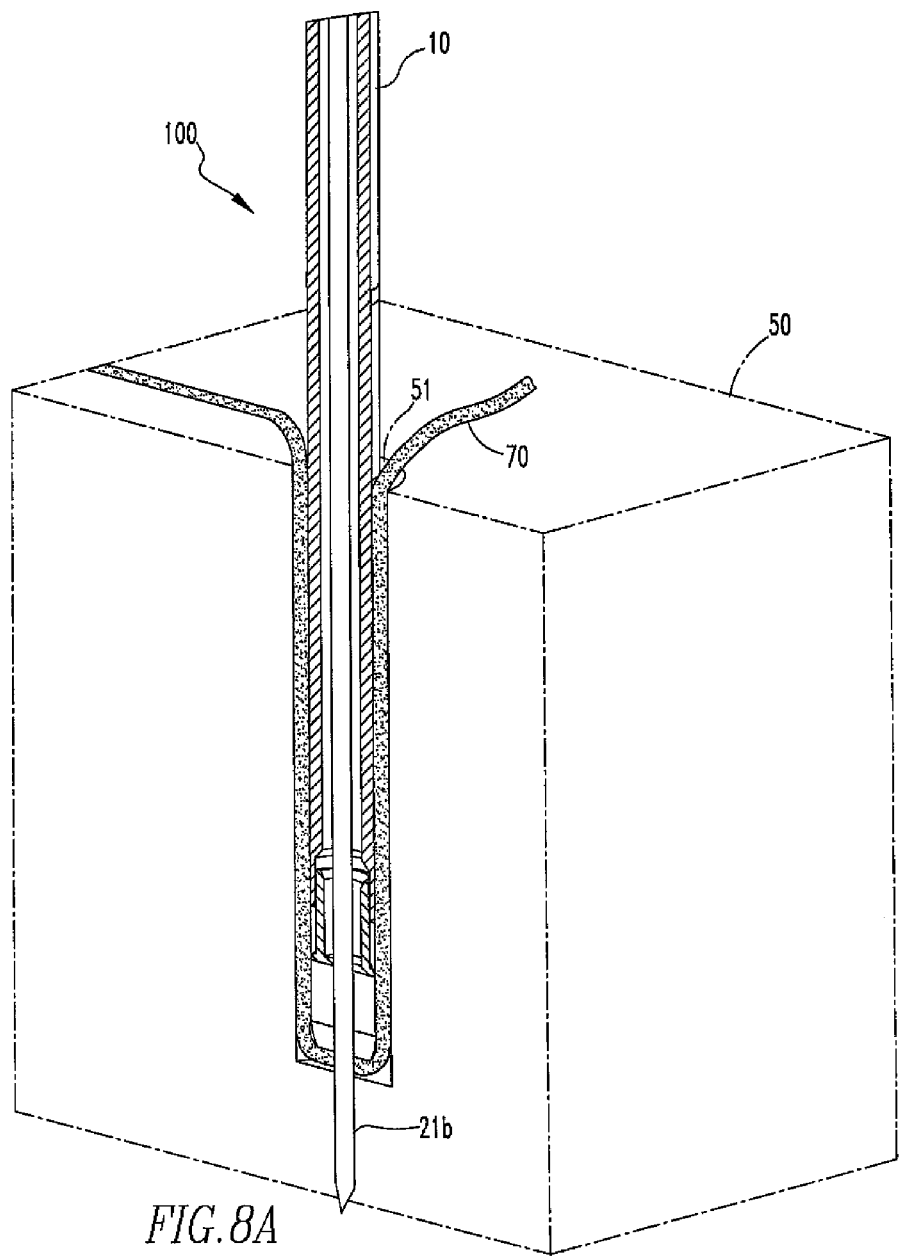
FIG. 8A shows a representation of area 100 of FIG. 8 with soft tissue (not shown in FIG. 8) having been inserted into the bone via the soft tissue manipulator assembly of FIG. 5A.

Once the reamer 60 and the drill bit 40 have been removed from the bone 50, the soft tissue manipulator instrument 10 is used to manipulate the soft tissue 70 and place the soft tissue 70 within the channel 13b. The shaft 12 of the instrument 10 and the soft tissue 70 are then placed within the hole 51 and the guide assembly 20 is placed within the cannulation 14 of the instrument 10 until the bottom portion 22b of the vice 22 abuts the handle 11 of the instrument 10, as shown in FIG. 8. At the same time, the distal portion 21b of the wire 21 is inserted through the soft tissue 70 and subsequently disposed within the bone 50 lying beneath the hole 51, as shown in FIG. 8A. The distal portion 21b of the wire 21 is inserted into the bone 50 by tapping the top portion 22a of the vice 22 with a mallet, or another striking force, until the bottom portion 22b abuts the handle 11. The vice 22 acts as a depth stop in limiting the depth of the distal portion 21b of the wire 21 into the bone 50. Other factors that limit the depth of the distal portion 21b into the bone 50 include, without limitation, the length of the wire 21, the length of the instrument 10, and the depth of the channel 22a.

Figure 9:
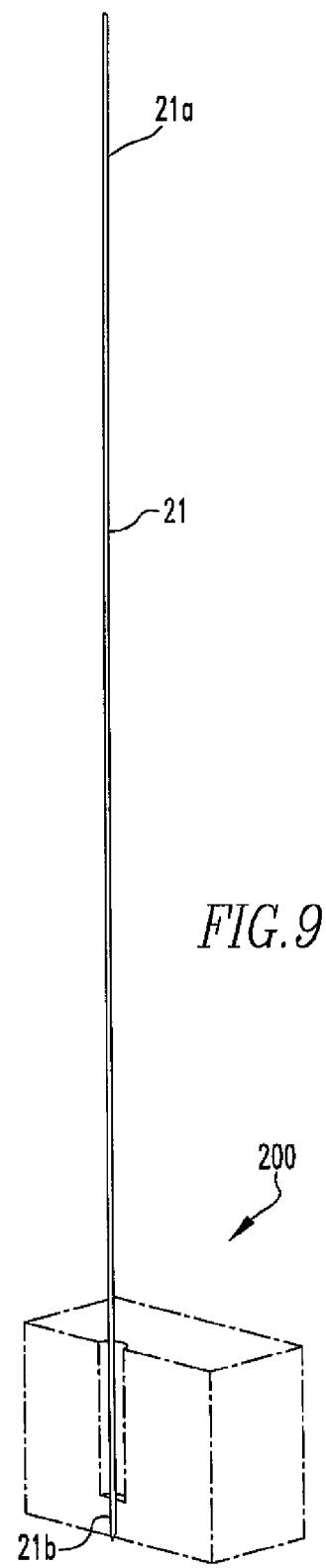
FIG. 9 shows disposal of the guide wire of the guide assembly of FIG. 4A within bone.
Figure 9A:
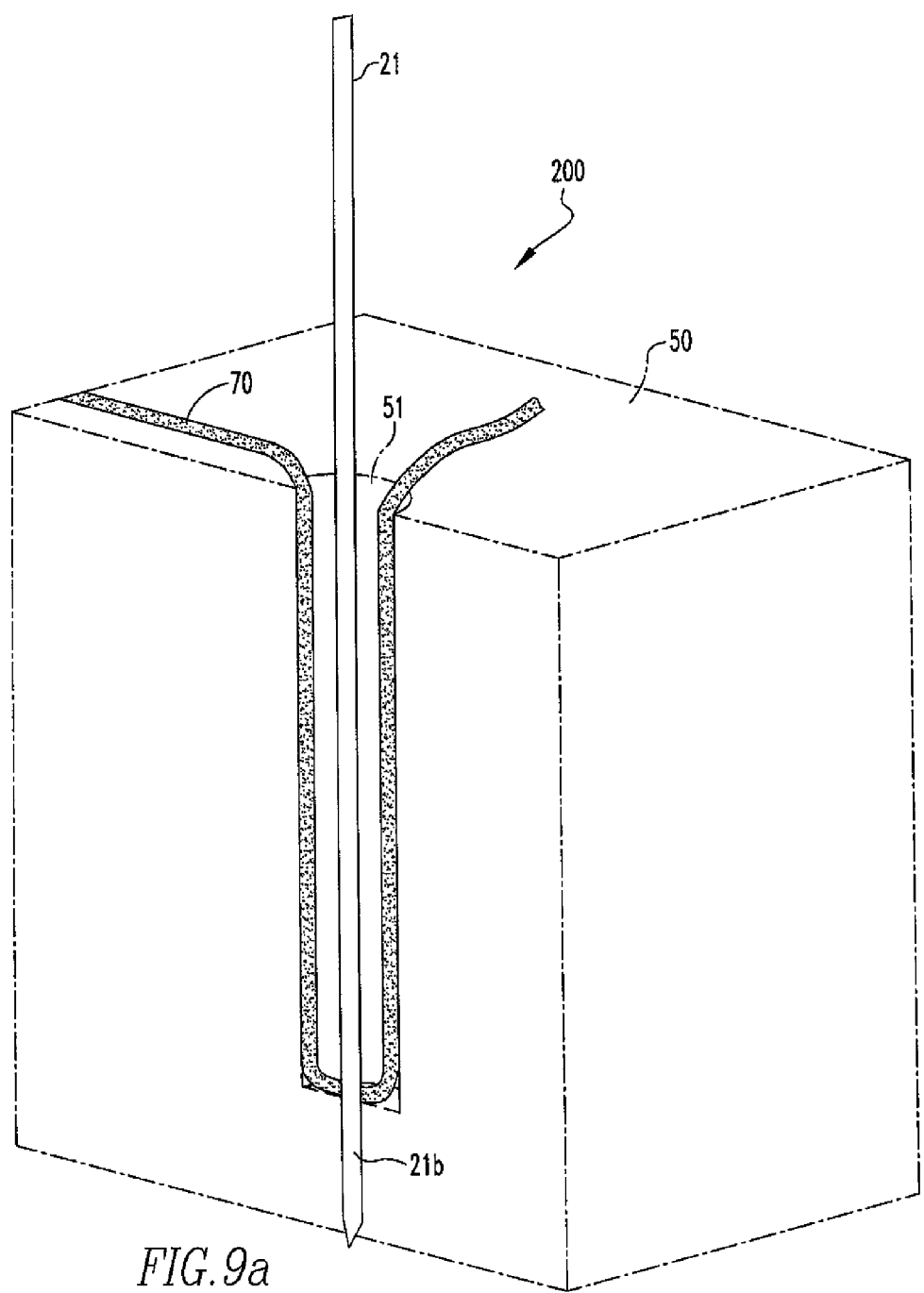
FIG. 9A shows a representation of area 200 of FIG. 9 with soft tissue (not shown in FIG. 9).

FIGS. 9 and 9A show that the vice 22 has been removed from the proximal portion 21a of the wire 21 by disengaging the pin 22g from the wire 21 and uncoupling the vice 22 from the proximal portion 21a. The instrument 10 has also been removed from the hole 51, thereby leaving the wire 21 alone in the hole 51.

Figure 10:
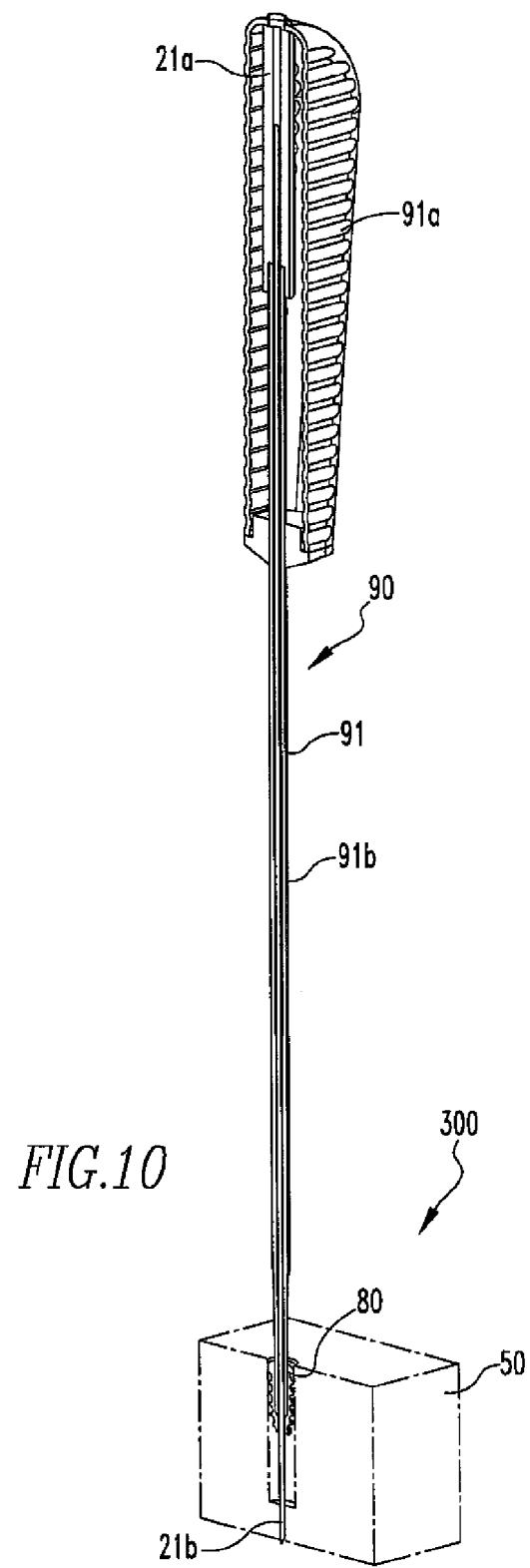
FIG. 10 shows insertion of a fixation device into bone via use of a driver.
Figure 10A:
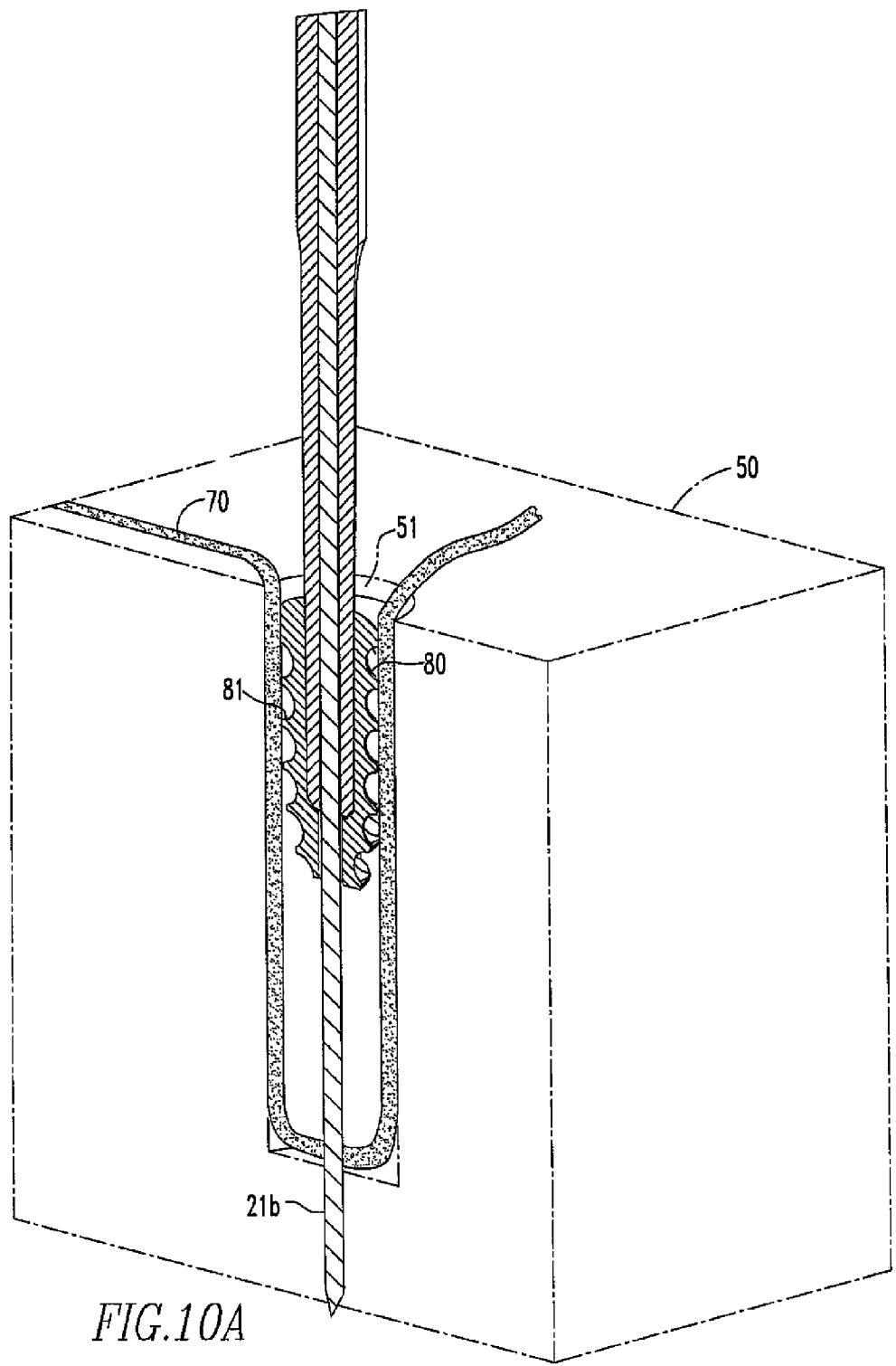
FIG. 10A shows a representation of area 300 of FIG. 10 with soft tissue (not shown in FIG. 10).
Figure 11:
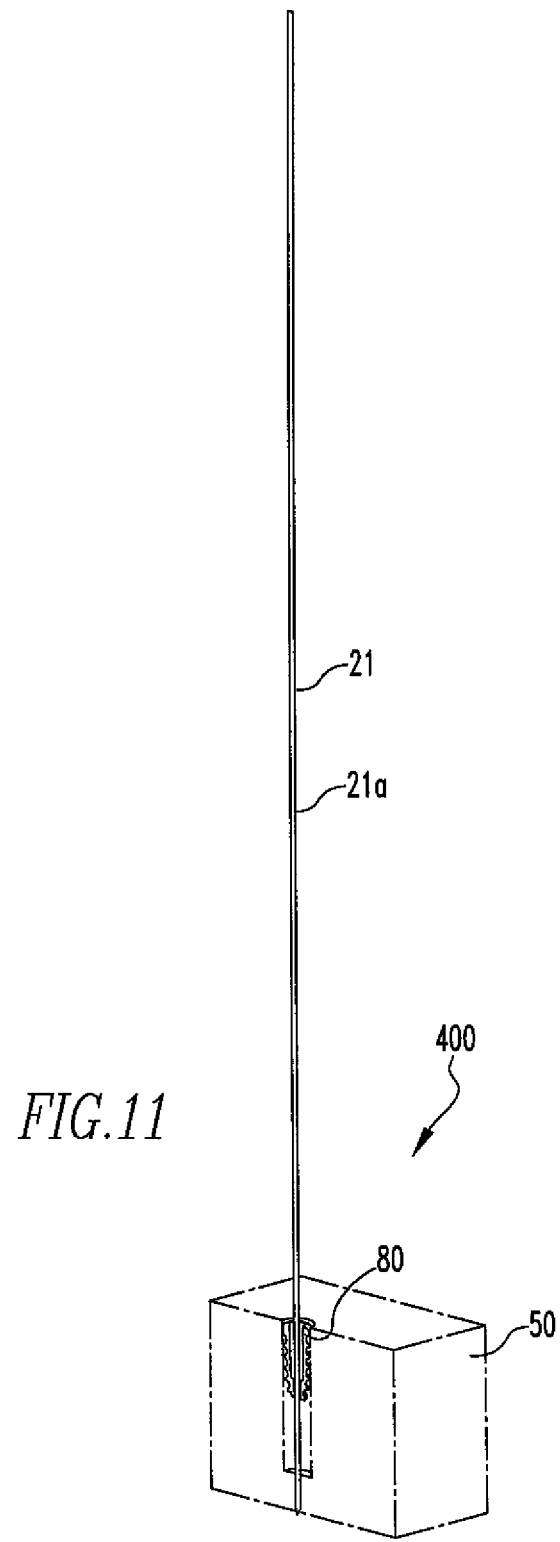
FIG. 11 shows disposal of the guide wire of the guide assembly of FIG. 4A and the fixation device of FIGS. 10-10A within bone.
Figure 11A:
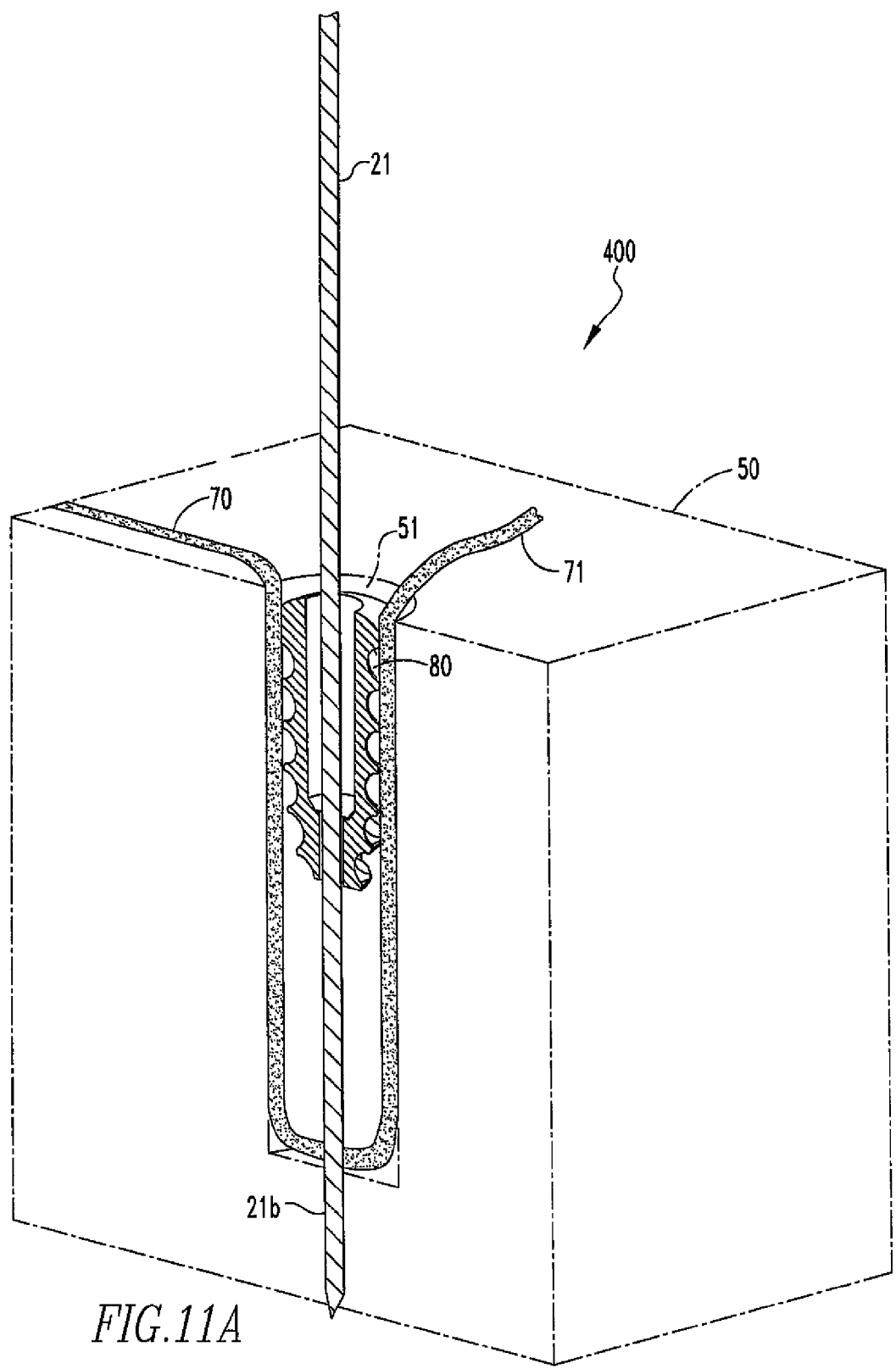
FIG. 11A shows a representation of area 400 of FIG. 11 with soft tissue (not shown in FIG. 11).
Figure 12:
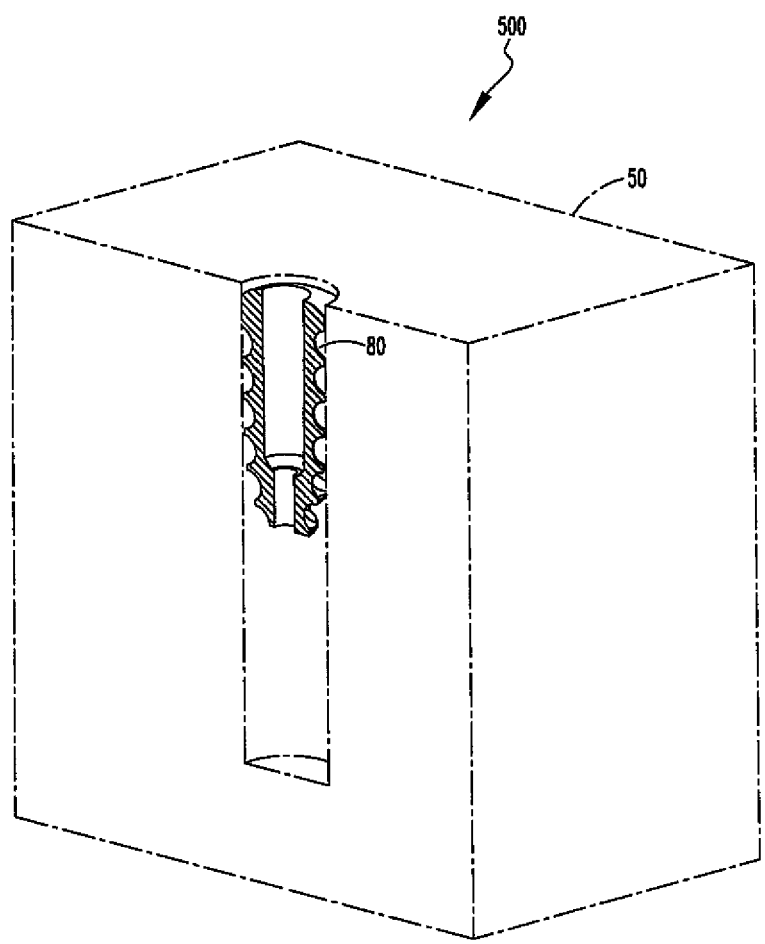
FIG. 12 shows disposal of the fixation device of FIGS. 10-10A within bone.
Figure 12A:
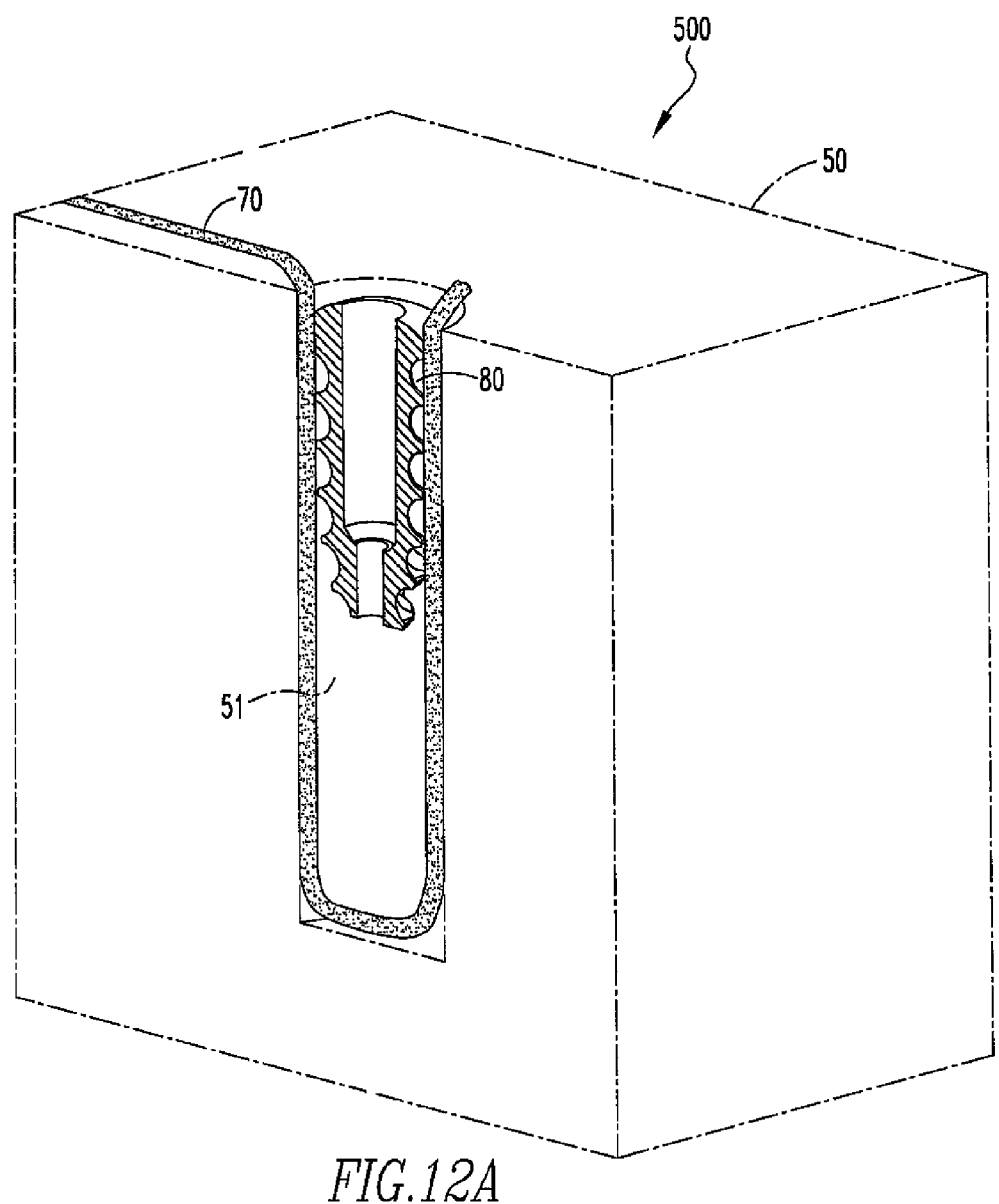
FIG. 12A shows a representation of area 500 of FIG. 12 with soft tissue (not shown in FIG. 12).

The wire 21 is subsequently used to guide the insertion of a fixation device 80, such as an interference screw, into the hole 51, as shown in FIGS. 10 and 10A. A driver assembly 90, which includes a cannulated driver 91 having a handle 91a and a shaft 91b coupled to the handle 91a and the cannulated fixation device 80 coupled to the shaft 91b, is disposed over the wire 21. The driver 91 is rotated to insert the device 80 into the hole 51, such that the threaded outer surface 81 of the device 80 is engaged with the soft tissue 70, thereby fixating the soft tissue 70 to the bone 50. After insertion of the device 80 into the hole 51, the driver 91 and the wire 21 are both removed from the bone 50, thereby leaving the device 80 within the hole, as shown in FIGS. 11-11A and 12-12A. The wire 21 is removed by placing the proximal portion 21a into the channel 22c of the vice 22, rotating the knob 22f to couple the assembly 22e to the wire 21, and then using the assembly 22e to remove the wire 21 from the hole 50. Other methods of removing the wire 21 are also within the scope of this disclosure.

The soft tissue manipulator instrument 10 and drill bit 40 are made from a biocompatible material, such as titanium, stainless steel, or other biocompatible material and via a machining process or other process known to one of skill in the art. A combination of processes may also be used to make the instrument 10 and drill bit 40. The cannulation 14 and channel 13b are formed during or after the machining process via a method, such as drilling. The markings 12b' and associated numbers are formed by a laser or another method and the threads 43 are formed via a machining process.

The guide assembly 20 and its components and the reamer 60 are also made from a biocompatible material, such as titanium, stainless steel, or other biocompatible material and via a machining process or other process known to one of skill in the art. A combination of processes may also be used to make the assembly 20 and reamer 60. The channel 22c, hole 22d, cannulation, and threads on the inner surface 22d' of the hole 22d, the distal portion 22g'' of the pin 22g, and the reamer 60 are formed during or after the machining process via a process, such as drilling or other process known to one of skill in the art.

The fixation device 80 is made from a resorbable polymer material. However, a metal material and other non-metal materials, either resorbable or non-resorbable, are also within the scope of this disclosure. In addition, the device 80 may be made via a molding process or other process known to one of skill in the art. The cannulation and threads on the outer surface 81 of the device 80 may be formed during the molding process or after the molding process by drilling or machining.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. An instrument with a proximal end and a distal end, the instrument configured to manipulate soft tissue during a soft tissue repair procedure, the instrument comprising:
    a cannulated instrument body;
    a first prong coupled to the cannulated instrument body, wherein the first prong is a most distal element of the instrument and is offset from a cross-sectional center of the cannulated instrument body; and
    markings on the instrument representing a measured distance from a distal end of the first prong to the markings.

2. The instrument of claim 1 wherein the cannulated instrument body includes a handle at its proximal end.

3. The instrument of claim 1 wherein the cannulated instrument body includes a shaft near its distal end.

4. The instrument of claim 1, further comprising a second prong coupled to the cannulated instrument body opposite from the first prong to form a channel between the first prong and the second prong, wherein the channel aligns at least in part with a cannulation of the cannulated instrument body.

5. The instrument of claim 4 wherein the second prong is substantially a mirror image of the first prong about a longitudinal axis of the cannulated instrument body.

6. The instrument of claim 4 wherein a diameter of the prongs is larger than a diameter of the instrument proximal of the prongs.

7. The instrument of claim 4 wherein there are markings on the instrument representing a measured distance from a distal end of the second prong to the markings.

8. The instrument of claim 4 wherein the first and second prongs have respective first axes parallel with a longitudinal axis of the cannulated instrument body, and the first and second prongs are generally rectangular in cross-section transverse to their respective first axes, and each of the first and second prongs has a longer length side of its respective rectangular cross-section that is oriented generally perpendicularly to the longitudinal axis of the cannulated instrument body.

9. An instrument with a proximal end and a distal end, the instrument configured to manipulate soft tissue during a soft tissue repair procedure, the instrument comprising:
   a cannulated instrument body;
   a first prong coupled to the cannulated instrument body, wherein the first prong is a most distal element of the instrument and is offset from a cross-sectional center of the cannulated instrument body;
   a second prong coupled to the cannulated instrument body opposite from the first prong to form a channel between the first prong and the second prong, wherein the channel aligns at least in part with a cannulation of the cannulated instrument body; and
   markings on the instrument representing a measured distance from a distal end of the first prong to the markings;
   wherein the first prong and the second prong are rounded and blunted at their respective distal ends to not readily penetrate bone when pushed against the bone.

10. The instrument of claim 9 wherein the cannulated instrument body includes a handle at its proximal end.

11. The instrument of claim 9 wherein the cannulated instrument body includes a shaft near its distal end.

12. The instrument of claim 11 wherein a diameter of the prongs is larger than a diameter of the shaft proximal of the prongs.

13. The instrument of claim 9 wherein the second prong is substantially a mirror image of the first prong about a longitudinal axis of the cannulated instrument body.

14. An instrument with a proximal end and a distal end, the instrument configured to manipulate soft tissue during a soft tissue repair procedure, the instrument comprising:
   a cannulated instrument body;
   a fork means at a distal end of the instrument for capturing soft tissue between a first prong of the fork and a second prong of the fork and aligning the soft tissue with a cannulation of the cannulated instrument body; and
   a depth determining means for measuring a distance from a distal end of the fork means to markings on the instrument.

15. The instrument of claim 14 wherein the cannulated instrument body includes a handle at its proximal end.

16. The instrument of claim 14 wherein the cannulated instrument body includes a shaft near its distal end.

17. The instrument of claim 16 wherein an outer diameter of the fork means is larger than the shaft proximal of the fork means.

18. The instrument of claim 14 wherein a channel is formed between the first prong of the fork and the second prong of the fork and the channel is substantially coaxially aligned with the cannulation of the cannulated instrument body.

19. An instrument with a proximal end and a distal end, the instrument configured to manipulate soft tissue during a soft tissue repair procedure, the instrument comprising:
   a cannulated instrument body;
   a first prong coupled to the cannulated instrument body, wherein the first prong is a most distal element of the instrument and is offset from a cross-sectional center of the cannulated instrument body;
   a second prong coupled to the cannulated instrument body opposite from the first prong to form a channel between the first prong and the second prong, wherein the channel aligns at least in part with a cannulation of the cannulated instrument body; and
   markings on the instrument representing a measured distance from a distal end of the second prong to the markings;
   wherein the first prong and the second prong are rounded and blunted at their respective distal ends to not readily penetrate bone when pushed against the bone.

20. The instrument of claim 19 wherein the cannulated instrument body includes a handle at its proximal end.

21. The instrument of claim 19 wherein the cannulated instrument body includes a shaft near its distal end.

22. The instrument of claim 21 wherein a diameter of the prongs is larger than a diameter of the shaft proximal of the prongs.

23. The instrument of claim 19 wherein the second prong is substantially a mirror image of the first prong about a longitudinal axis of the cannulated instrument body.

* * * * *